United States Patent
Sato

(10) Patent No.: US 6,488,945 B2
(45) Date of Patent: Dec. 3, 2002

(54) LIQUID COSMETIC

(75) Inventor: Hiroshi Sato, Fujioka (JP)

(73) Assignee: Mitsubishi Pencil Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/910,493

(22) Filed: Jul. 19, 2001

(65) Prior Publication Data

US 2002/0051756 A1 May 2, 2002

Related U.S. Application Data

(63) Continuation of application No. 09/501,759, filed on Feb. 10, 2000, now abandoned.

(30) Foreign Application Priority Data

Feb. 23, 1999 (JP) .............................................. 11-45204

(51) Int. Cl.[7] .......................... A61K 7/00; A61K 7/021; A61K 31/74
(52) U.S. Cl. ...................... 424/401; 424/63; 424/78.03
(58) Field of Search ........................ 424/401, 63, 78.03

(56) References Cited

U.S. PATENT DOCUMENTS

| 4,975,371 A | * | 12/1990 | Kawaguchi | 435/101 |
| 5,688,831 A | | 11/1997 | El-Nokaly et al. | 514/938 |
| 5,858,928 A | * | 1/1999 | Aubert et al. | 507/128 |
| 5,928,660 A | * | 7/1999 | Kobayashi et al. | 424/401 |
| 6,027,739 A | * | 2/2000 | Nichols | 424/401 |
| 6,117,434 A | * | 9/2000 | Oyama et al. | 424/401 |
| 6,251,411 B1 | * | 6/2001 | Kishida et al. | 424/401 |

FOREIGN PATENT DOCUMENTS

| JP | 6-57290 | | 1/1994 |
| JP | 2-12924 | | 7/1997 |
| JP | 9-175924 | * | 7/1997 |
| JP | 9-175924 | | 8/1997 |
| JP | 10-231233 | | 2/1998 |

* cited by examiner

Primary Examiner—Thurman K. Page
Assistant Examiner—S. Tran
(74) Attorney, Agent, or Firm—Darby & Darby

(57) ABSTRACT

Provided is a liquid cosmetic characterized by comprising 5 to 25% by weight of a pearl pigment containing at least mica, mica titan or a surface-treated substance thereof and 0.2 to 2.0% by weight of an anionic high molecular compound as a structural viscosity-providing agent, wherein the non-Newtonian viscosity index (n) falls in a range of $0.16 \leq n \leq 0.28$, and the viscosity satisfies the following condition (A):

| (A) shear rate ($S^{-1}$) | viscosity (mPa · s) |
|---|---|
| 3.83 | 1500 to 5000 |
| 19.20 | 500 to 1500 |
| 38.30 | 300 to 700 |
| 76.80 | 150 to 400 |
| 383.00 | 50 to 100. |

4 Claims, No Drawings

LIQUID COSMETIC

This application is a continuation of 09/501,759 filed Feb. 10, 2000, which has been abandoned.

BACKGROUND OF THE INVENTION

1. Field of the Invention

The present invention relates to a liquid cosmetic, specifically to a water based liquid cosmetic. More specifically, the present invention relates to a liquid cosmetic which is suited to a liquid cosmetic applicator using a brush as an applying means and containing therein a water based liquid cosmetic, particularly to a liquid makeup cosmetic which is suited to eye makeup.

2. Description of the Related Art

Disclosed in Japanese Patent Publication No. Hei 2-12924 is a liquid eye makeup cosmetic which contains lecithin such as soybean phospholipid and egg yolk phospholipid and hydrogenation products thereof, a nonionic surfactant and an inorganic pigment and which has a viscosity of 3 to 300 cps at 25° C. A colorant is not specifically restricted.

Further, disclosed in Japanese Patent Application Laid-Open No. Hei 10-231233 is an eye makeup cosmetic which uses as a colorant, titan black without using black iron oxide having a difficulty in dispersion due to a magnetism thereof and carbon black having an anxiety of carcinogenesis and which provides a sufficiently high density of the drawn lines and can be wiped off well. However, nothing is referred to as long as a pearl pigment is concerned, and an eye makeup cosmetic comprising lecithin or a hydrogenation product thereof and a nonionic surfactant having an HLB value of 10 or more is disclosed.

Provided in Japanese Patent Application Laid-Open No. Hei 6-57290 is a gelatinous cosmetic which is obtained from a composition comprising (A) an N-long-chain acyl acidic amino acid salt having an acyl group having 8 to 22 carbon atoms and (B) water in a weight ratio (A)/(B) falling in a range of 5/95 to 30/70 and which has a thixotropy, and provided are cosmetics such as cleansing cream and the like which are easy to apply and have a good use feeling and which have a low stimulation to skins and can readily contain a lot of oil components.

In the case of a liquid cosmetic having a low viscosity, pulverization of inorganic pigments into fine powders makes it possible to inhibit them from settling down, but involved are the problems that the masking property is reduced and the good color tone is not obtained. Further, when a thickener is added in order to prevent settling of inorganic pigments, an expected thickening effect is not obtained due to electrolytes depending the kind of the thickener, and the fluidity is lost due to gelation or there has been a problem on the stability with the passage of time. However, provided in Japanese Patent Application Laid-Open No. Hei 9-175924 is a liquid cosmetic in which the problems described above have been solved by compounding an inorganic pigment dispersed with polysaccharides, a clay mineral, a water-soluble organic solvent and water.

A pearl pigment is suitably compounded for obtaining clear and brilliant finishing with makeup cosmetics, particularly eye makeup cosmetics. In a water based dispersion, however, a pearl pigment settles down quickly because of the coarse particles thereof as compared with those of ordinary organic and inorganic pigments. Further, because of the oblate particle form thereof, the pigment once settled is liable to form a cake and can not be redispersed easily even by stirring in using.

Because of this reason, there has not so far been available, a liquid cosmetic applicator using a brush as an applying member and containing therein a water based liquid cosmetic, in which a pearl pigment is compounded and in which a brilliant developed color is obtained and an ordinarily satisfactory quality is maintained.

Further, in a liquid cosmetic applicator using a brush as an applying member, use of conventional liquid cosmetics increases the amount of the cosmetics contained in the applying member since the applying member is a brush, and there has been the inconvenience that impact and vibration exerted in carrying allows the body in the periphery of the applying member and the inside of the cap to be contaminated, which in turn contaminates environment such as hands and fingers when the user uses it.

SUMMARY OF THE INVENTION

The present invention provides a pearl pigment-blended liquid cosmetic which is excellent in a stability against settling with the passage of time and which can readily be redispersed by stirring even if the pigment settles down, for example, a pearl pigment-blended, water based liquid cosmetic which is suited for using with a liquid cosmetic applicator of a type using a brush as an applying member and containing therein a water based liquid cosmetic.

Intensive researches repeated by the present inventors in order to develop a liquid cosmetic which is suited to a liquid cosmetic applicator containing therein a water based liquid cosmetic and using a brush as an applying member have resulted in finding that the subjects described above can be achieved by blending a pearl pigment containing at least mica, mica titan or a surface-treated substance thereof and composed made substantially of an inorganic substance, and an anionic high molecular compound as a structural viscosity-providing agent and by allowing the specific non-Newtonian viscosity index (n) and the viscosity at a prescribed shear rate to be maintained in the specific ranges, and coming to complete the present invention based on the knowledge described above.

That is, the present invention relates to a liquid cosmetic characterized by comprising 5 to 25% by weight of a pearl pigment composed made substantially of an inorganic substance, said pearl pigment containing at least mica, mica titan or a surface-treated substance thereof, and 0.2 to 2.0% by weight of an anionic high molecular compound, wherein the specific non-Newtonian viscosity index (n) falls in a range of $0.16 \leq n \leq 0.28$, and the viscosity satisfies the following condition (A):

| (A) shear rate $(S^{-1})$ | viscosity $(mPa \cdot s)$ |
|---|---|
| 3.83 | 1500 to 2500 |
| 19.20 | 500 to 700 |
| 38.30 | 300 to 450 |
| 76.80 | 150 to 250 |
| 383.00 | 50 to 100 |

Preferably, the pearl pigment contained in the liquid cosmetic described above contains a surface-treated substance subjected to surface treatment with iron oxide.

More preferably, the anionic high molecular compound contained in the liquid cosmetic described above is xanthan gum.

Still more preferably, these liquid cosmetics display sufficiently the effects thereof when using a liquid cosmetic applicator using a brush as an applying member and containing therein a liquid cosmetic.

DETAILED DESCRIPTION OF PREFERRED EMBODIMENTS

In the cosmetic of the present invention, at least mica, mica titan or a surface-treated substance thereof is contained in the pearl pigment used. Such pearl pigment comprises substantially an inorganic substance and has a high safety to a human body.

The surface-treated substance of mica or mica titan includes, for example, carmine-coated mica titan, carmine•Prussian blue-coated mica titan, black iron oxide-coated mica titan, black iron oxide•carmine-coated mica titan, black iron oxide•Prussian blue-coated mica titan, Prussian blue-coated mica, Prussian blue-coated mica titan, red iron oxide-coated mica, red iron oxide-coated mica titan, red iron oxide•carmine-coated mica titan, red iron oxide•black iron oxide-coated mica titan, red iron oxide•Prussian blue-coated mica titan, red iron oxide•black iron oxide•Prussian blue-coated mica titan and $N^\epsilon$-lauroyl-L-lysine-coated mica.

Further, bismuth oxychloride and the like can be compounded as a pearl pigment other than mica and mica titan.

The pearl pigments described above may be used alone or in combination of two or more kinds thereof.

The blending amount of the pearl pigment is preferably 5 to 25% by weight based on the whole amount of the cosmetic in order to obtain the good drawn lines, applying performance and use characteristics.

Further, the pearl pigments described above may be used in combination with inorganic pigments. The preferred inorganic pigments include, for example, black iron oxide, yellow iron oxide, chromium oxide, ultramarine, Prussian blue, zinc oxide, aluminum oxide, silicon dioxide, titanium oxide, magnesium oxide, chromium hydroxide, calcium carbonate, magnesium carbonate, Titan Yellow and red iron oxide.

The blending amount of the inorganic pigments shall not specifically be restricted, and the optional amount can be blended in a range of the viscosity of the cosmetic according to the present invention.

In addition to the pearl pigments and inorganic pigments described above, there can be used as well, if necessary, pearl pigments (fish scales and N'-lauroyl-L-lysine-coated talc) other than those designated above, organic pigments and various dyes.

In the cosmetic of the present invention, an anionic high molecular compound is used as a dispersant for the pearl pigment described above. This anionic high molecular compound includes, for example, tragacanth gum, guar gum, xanthan gum, gelatin, gum arabic, caraya gum, quince seed, carrageenan, sodium alginate, carboxymethyl cellulose, poly(sodium acrylate) and a maleic acid resin. They each may be used alone or in combination of two or more kinds thereof. The blending amount of the anionic high molecular compound is selected so that the viscosity of the resulting cosmetic falls in a prescribed range. The blending amount of the anionic high molecular compound is varied according to the kind and the combination of the anionic high molecular compounds used and is preferably 0.2 to 2.0% by weight based on the whole amount of the cosmetic.

In addition thereto, the liquid cosmetic of the present invention can be blended with components the examples of which are given below.

Phospholipid added as a dispersion stabilizer includes, for example, various lecithins such as soybean phospholipid and egg yolk phospholipid and hydrogenation products thereof, and a chelating agent includes, for example, ethylenediaminetetraacetic acid, ethylenediaminehydroxyethyltriacetic acid, and monosodium salts, disodium salts and trisodium salts thereof.

Paraben added as a preservative includes, for example, methyl paraoxybenzoate, ethyl paraoxybenzoate, propyl paraoxybenzoate, butyl paraoxybenzoate and isopropyl paraoxybenzoate.

Polyhydric alcohol added as a moisturizer includes, for example, 1,3-butylene glycol, 1,4-butylene glycol, ethylene glycol, diethylene glycol, polyethylene glycol, propylene glycol, dipropylene glycol and glycerin.

A surfactant added as a dispersant includes, for example, polyglycerin esters of saturated or unsaturated fatty acids, polyoxyethylene alkyl ethers, polyoxyethylene sorbitan fatty acid esters, polyoxyethylene sorbit fatty acid esters, polyoxyethylene glycerin fatty acid esters, polyethylene glycol fatty acid esters, polyoxyethylene phytosterols, polyoxyethylene phytostanols, polyoxyethylene polyoxypropylene alkyl ethers, polyoxyethylene alkylphenyl ethers, polyoxyethylene castor oil, polyoxyethylene hydrogenated castor oil, polyoxyethylene alkyl ether acetates, and polyoxyethylene alkylphosphates.

Further, in the cosmetic of the present invention, other pigment particle-dispersing agents, and optional additives which are used for the purpose of providing a viscosity-controlling property, a fixing property, a water resistance, an oil resistance, a sweat resistance, a drying property, an antiseptic property and the like in addition to the components described above can be blended, if necessary, as long as they do not bring disadvantages to the dispersion system. In this case, it is necessary that the blending amounts thereof have to be controlled so that the above cosmetic has a non-Newtonian viscosity index (n) falling in a range of $0.16 \leq n \leq 0.28$ and a viscosity falling in a range of the condition (A) described above.

The non-Newtonian viscosity index (n) and the viscosity of the liquid cosmetic of the present invention can be controlled to the ranges described above by suitably selecting the blending amount of the anionic high molecular compound. That is, the suitable blending amount of the anionic high molecular compound is varied according to the kind and the combination of the anionic high molecular compounds and, for example, when xanthan gum and tragacanth gum are used in combination, the blending amount thereof is set preferably to 0.2 to 2.0% by weight, more preferably 0.6 to 1.0% by weight, whereby the non-Newtonian viscosity index (n) and the viscosity can be controlled to the ranges described above.

The non-Newtonian viscosity index (n) and the viscosity are measured on a fixed temperature condition of 25° C.

The liquid cosmetic of the present invention can be produced according to a conventional process, and one example thereof includes a process in which a pearl pigment is mixed and dispersed with dispersants (an anionic high molecular compound and a surfactant), and then additives such as a preservative, a moisturizer, a chelating agent and the like are blended while stirring.

The liquid cosmetic of the present invention is suited particularly as a water based cosmetic, for example, an eye makeup cosmetic, but it shall not be restricted thereto and can widely be applied to the whole liquid cosmetics such as, for example, lip sticks, foundations and the like.

Further, the liquid cosmetic of the present invention is a water based cosmetic which is suited particularly to a liquid cosmetic applicator of a type using a brush as an applying member and containing therein a water based liquid cosmetic.

EXAMPLES

The present invention shall more specifically be explained below with reference to examples, but the present invention shall by no means be restricted by these examples.

Examples 1, 2 and 3 and Comparative Examples 1 and 2

The liquid cosmetics of the present invention (Examples 1 to 3) and the liquid cosmetics of comparison (Comparative Examples 1 and 2) were prepared in the compositions and the blending amounts shown in Table 1 and tested by the following test methods. The results thereof are shown together in Table 1.

Usability test:
The liquid cosmetics prepared in Examples 1 to 3 and Comparative Examples 1 and 2 were charged into cosmetic vessels of a brush pen type, and five lines having a width of 1 to 2 mm and a length of about 5 cm were drawn on the back of a hand to evaluate the drawing state and the density of the drawn lines.

Evaluation:
AA: easy to draw at a sufficiently high density
A: a little starving and feathering present and judged to fall within a practical area
B: starving and feathering present and felt unsatisfactory Settling stability test:
The liquid cosmetics prepared in Examples 1 to 3 and Comparative Examples 1 and 2 were taken into test tubes having a screw top and stoppered tightly. After leaving them standing for one month, the presence of separation of the liquids was observed and evaluated.

Evaluation:
AAA: no change
AA: supernatant of about 1 mm produced
A: such a little separation as color separation present
B: distinct separation present Redispersibility test:
The liquid cosmetics prepared in Examples 1 to 3 and Comparative Examples 1 and 2 were taken into test tubes having a screw top, and balls for stirring the liquids were put therein. They were left standing at 50° C. for one month. Then, they were shaken with a hand to observe the movement of the balls and evaluate it.

Evaluation:
AA: ball moves soon by shaking once or twice
A: ball moves by shaking 3 to 9 times
B: have to be shaken 10 times or more until the stirring ball starts moving

TABLE 1

| | | | (blending amount: % by weight) | | | | |
|---|---|---|---|---|---|---|---|
| | | | Gum amount | | | Gum amount | |
| | | | Optimum | Large | Small | Large | Small |
| | | | | Example | | Comparative Example | |
| | | | 1 | 2 | 3 | 1 | 2 |
| 1 | Pearl pigment | Black iron oxide-coated mica titan | | | 10 | | 10 |
| 2 | | Iron oxide-coated mica titan | 10 | 10 | 10 | | |
| 3 | Stabilizer | Hydrogenated egg yolk lecithin | 0.5 | 0.5 | 0.5 | 0.5 | 0.5 |
| 4 | | Polyethylene glycol fatty acid ester | 0.5 | 0.5 | 0.5 | 0.5 | 0.5 |
| 5 | Dispersant | Alkyl acrylate copolymer emulsion | 15 | 15 | 15 | 15 | 15 |
| 6 | | Xanthan gum | 0.5 | 0.7 | 0.4 | 0.8 | 0.3 |
| 7 | | Tragacanth gum | 0.2 | 0.3 | 0.2 | 0.4 | 0.2 |
| 8 | Chelating agent | Ethylenediaminetetraacetic acid | 0.3 | 0.3 | 0.3 | 0.3 | 0.3 |
| 9 | | Trisodium ethylenediamine-hydroxyethyltriacetate | 0.4 | 0.4 | 0.4 | 0.4 | 0.4 |
| 10 | Preservative | Sodium dehydroacetate | 0.1 | 0.1 | 0.1 | 0.1 | 0.1 |
| 11 | | Methyl paraoxybenzoate | 0.3 | 0.3 | 0.3 | 0.3 | 0.3 |
| 12 | | Ethyl paraoxybenzoate | 0.2 | 0.2 | 0.2 | 0.2 | 0.2 |
| 13 | | Propyl paraoxybenzoate | 0.1 | 0.1 | 0.1 | 0.1 | 0.1 |
| 14 | | Butyl paraoxybenzoate | 0.05 | 0.05 | 0.05 | 0.05 | 0.05 |
| 15 | Moisturizer | 1,3-Butylene glycol | 10 | 10 | 10 | 10 | 10 |
| 16 | Purified water | balance | balance | balance | balance | balance | |
| 17 | Non-Newtonian viscosity index (n) | | 0.209 | 0.172 | 0.253 | 0.15 | 0.292 |
| 18 | Viscosity | Shear rate (/s) | | | | | |
| | | 3.83 | 2700 cp | 4450 cp | 1720 cp | 6360 cp | 1150 cp |
| | | 19.2 | 650 cp | 1160 cp | 533 cp | 1580 cp | 391 cp |
| | | 38.3 | 406 cp | 640 cp | 310 cp | 868 cp | 232 cp |
| | | 76.8 | 225 cp | 358 cp | 180 cp | 475 cp | 138 cp |
| | | 383 | 70 cp | 99 cp | 56 cp | 127 cp | 45 cp |

TABLE 1-continued

|  | (blending amount: % by weight) | | | | |
|---|---|---|---|---|---|
|  | Gum amount | | | Gum amount | |
|  | Optimum | Large | Small | Large | Small |
|  | Example | | | Comparative Example | |
|  | 1 | 2 | 3 | 1 | 2 |
| 19 Usability | AA | AA | AA | B | A |
| 20 Settling stability | AAA | AAA | AA | AAA | B |
| 21 Redispersibility | AA | AA | AA | AA | B |

(Measuring apparatus: EMD type viscometer, brand name VISCONIC EMD. R manufactured by Tokyo Keiki Co., Ltd.)

What is claimed is:

1. A liquid cosmetic composition comprising
   5 to 25% by weight of a pearl pigment, said pearl pigment comprising an inorganic substance and mica, mica titan or a surface-treated substance thereof; and
   0.6 to 1% by weight of an anionic high molecular compound selected from the group consisting of tragacanth gum, guar gum, xanthan gum, gelatin, gum arabic, caraya gum, quince seed, carrageenan, sodium alginate, carboxymethyl cellulose, poly(sodium acrylate) and maleic acid resin;
   wherein said composition has a non-Newtonian viscosity index (n) in a range of $0.16 \leq n \leq 0.28$, and a viscosity rate of:

| (A) shear rate ($S^{-1}$) | viscosity (mPa · s) |
|---|---|
| 3.83 | 1500 to 5000 |
| 19.20 | 500 to 1500 |
| 38.30 | 300 to 700 |
| 76.80 | 150 to 400 |
| 383.00 | 50 to 100. |

2. The liquid cosmetic composition of claim 1, wherein the pearl pigment contains a surface-treated substance subjected to surface treatment with iron oxide.

3. The liquid cosmetic composition of claim 1 or 2, wherein the anionic high molecular compound is xanthan gum.

4. A liquid cosmetic applicator comprising a brush and the liquid cosmetic composition of claim 1 or 2.

* * * * *